United States Patent
Finnestad et al.

(10) Patent No.: US 8,096,414 B2
(45) Date of Patent: Jan. 17, 2012

(54) MEDICAL IMPLEMENT DISPENSING AND DISPOSAL SYSTEM

(75) Inventors: Mark Brian Finnestad, Franklin, MA (US); Michael Sansoucy, Wrentham, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 328 days.

(21) Appl. No.: 11/933,715

(22) Filed: Nov. 1, 2007

(65) Prior Publication Data

US 2009/0114671 A1    May 7, 2009

(51) Int. Cl.
B65D 83/10 (2006.01)
B65D 69/00 (2006.01)
B65H 1/00 (2006.01)

(52) U.S. Cl. ............ 206/366; 221/34; 221/97; 221/102; 221/101; 221/33; 221/46; 206/370; 206/365; 206/364; 206/362; 206/216; 206/233; 206/499; 206/812; 202/908; 220/908; 312/34.4; 312/211; 232/43.2

(58) Field of Classification Search .................... 221/34, 221/97, 102, 101, 33, 46; 206/366, 370, 206/365, 364, 362, 216, 233, 499, 812; 202/908; 220/908; 312/34.4, 211; 232/43.2
See application file for complete search history.

(56) References Cited

U.S. PATENT DOCUMENTS

| | | | |
|---|---|---|---|
| 3,889,804 A | 6/1975 | Ravich | |
| 4,809,850 A | 3/1989 | Laible et al. | |
| 4,867,268 A | 9/1989 | Ulert | |
| 5,002,197 A * | 3/1991 | Ponsi | 220/255 |
| 5,005,727 A * | 4/1991 | Roth | 220/495.09 |
| 5,048,720 A * | 9/1991 | Hoke | 221/198 |
| 5,084,028 A | 1/1992 | Kennedy et al. | |
| 5,097,950 A | 3/1992 | Weiss et al. | |
| 5,107,990 A * | 4/1992 | Wicherski et al. | 206/366 |
| 5,143,210 A | 9/1992 | Warwick et al. | |
| 5,152,394 A * | 10/1992 | Hughes | 206/366 |
| 5,251,783 A * | 10/1993 | Gringer | 221/102 |
| 5,277,312 A * | 1/1994 | Vumbaca | 206/366 |
| 5,405,043 A | 4/1995 | Meloney | |
| 5,494,158 A | 2/1996 | Erickson | |
| 5,662,235 A | 9/1997 | Nieto | |
| 5,706,942 A | 1/1998 | Vila et al. | |

(Continued)

FOREIGN PATENT DOCUMENTS

| | | |
|---|---|---|
| DE | 538682 C | 11/1931 |
| DE | 9214287 U1 | 1/1993 |
| EP | 1449491 A | 8/2004 |
| GB | 2275673 A | 9/1994 |
| WO | WO 91/01920 | 2/1991 |
| WO | WO 2005/120610 | 12/2005 |

OTHER PUBLICATIONS

International Search Report dated Sep. 1, 2006, application No. PCT/US2006/016736.

(Continued)

*Primary Examiner* — Gene O. Crawford
*Assistant Examiner* — Rakesh Kumar
(74) *Attorney, Agent, or Firm* — Lisa E. Winsor, Esq.

(57) ABSTRACT

A medical implement dispensing and disposal system. The medical implement dispensing and disposal system comprises a container having an open end with a dispensing chamber and a disposal chamber defined within the container. A cover is configured to substantially close the open end of the container. The cover defines a disposal opening in communication with the disposal chamber. A dispensing opening is defined in either the container or cover and in communication with the dispensing chamber. A biasing assembly is positioned in the dispensing chamber and configured to provide a biasing force toward the dispensing opening.

16 Claims, 5 Drawing Sheets

U.S. PATENT DOCUMENTS

| | | | |
|---|---|---|---|
| 5,740,909 A | 4/1998 | Nazare et al. | |
| 5,878,899 A | 3/1999 | Manganiello et al. | |
| 6,685,017 B2 * | 2/2004 | Erickson | 206/366 |
| 6,702,147 B2 * | 3/2004 | Ashford | 221/34 |
| 6,902,083 B1 | 6/2005 | Michael et al. | |
| 6,923,318 B1 * | 8/2005 | Erickson et al. | 206/366 |
| 7,513,363 B2 * | 4/2009 | Brown et al. | 206/366 |
| 7,556,149 B2 * | 7/2009 | Erickson et al. | 206/366 |
| 7,694,822 B2 * | 4/2010 | Sullivan et al. | 206/571 |
| 7,815,046 B2 * | 10/2010 | Sansoucy et al. | 206/366 |
| 2002/0190073 A1 | 12/2002 | Hewett | |
| 2003/0132129 A1 | 7/2003 | Erickson | |
| 2003/0226851 A1 | 12/2003 | Antebi | |
| 2003/0226879 A1 | 12/2003 | Auclair et al. | |
| 2005/0189372 A1 * | 9/2005 | Fenton | 221/231 |
| 2005/0269227 A1 * | 12/2005 | Erickson et al. | 206/366 |
| 2009/0114667 A1 * | 5/2009 | Sansoucy et al. | 221/34 |

OTHER PUBLICATIONS

International Search Report corresponding to Application No. PCT/US2006/016320 dated Sep. 29, 2006.

European Search Report issued by European Patent office in co-pending EP Application No. EP08253433.0 mailed on Feb. 4, 2010.

* cited by examiner

MEDICAL IMPLEMENT DISPENSING AND DISPOSAL SYSTEM

FIELD OF THE INVENTION

The present invention relates generally to medical waste containers and more specifically to containers for the safe disposal of medical implements.

BACKGROUND OF THE INVENTION

A variety of containers have been developed for the collection and storage of needle syringes, sharps and other medical implements. A primary function of the containers is to provide a rigid enclosure that protects individuals from becoming injured by an exposed sharps. This function is especially significant in the handling of used sharps during disposal. Used sharps that are not properly contained pose a risk of serious injury to personnel who handle the used sharps. Accidental contact with a used needle can result in the transmission of various pathogens, including human immunodeficiency virus (HIV). In view of the risks associated with exposed sharps, sharps containers provide a safe way to store sharps during transport and disposal.

SUMMARY OF THE INVENTION

According to an aspect of the invention, a medical implement dispensing and disposal system is provided. The medical implement dispensing and disposal system comprises a container having an open end with a dispensing chamber and a disposal chamber defined within the container. A cover is configured to substantially close the open end of the container. The cover defines a disposal opening in communication with the disposal chamber. A dispensing opening is defined in either the container or cover and in communication with the dispensing chamber. A biasing assembly is positioned in the dispensing chamber and configured to provide a biasing force toward the dispensing opening.

In another aspect of the invention, the biasing assembly includes a platform positioned within the dispensing chamber. A biasing member is positioned between a bottom surface of the container and the platform.

In another aspect, the invention provides a medical implement dispensing and disposal system comprising a container and a cover. The container has an open end with a dispensing chamber and a disposal chamber defined within the container. The cover is configured to substantially close the open end of the container. The cover defines a disposal opening in communication with the disposal chamber and a dispensing opening in communication with the dispensing chamber. A biasing assembly is positioned in the dispensing chamber and configured to provide a biasing force toward the dispensing opening.

In another aspect of the invention, the cover includes a flexible flap extending across at least a portion of the dispensing opening. In at least one embodiment, the flexible flap has a rigidity greater than the biasing force.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Figure 1:
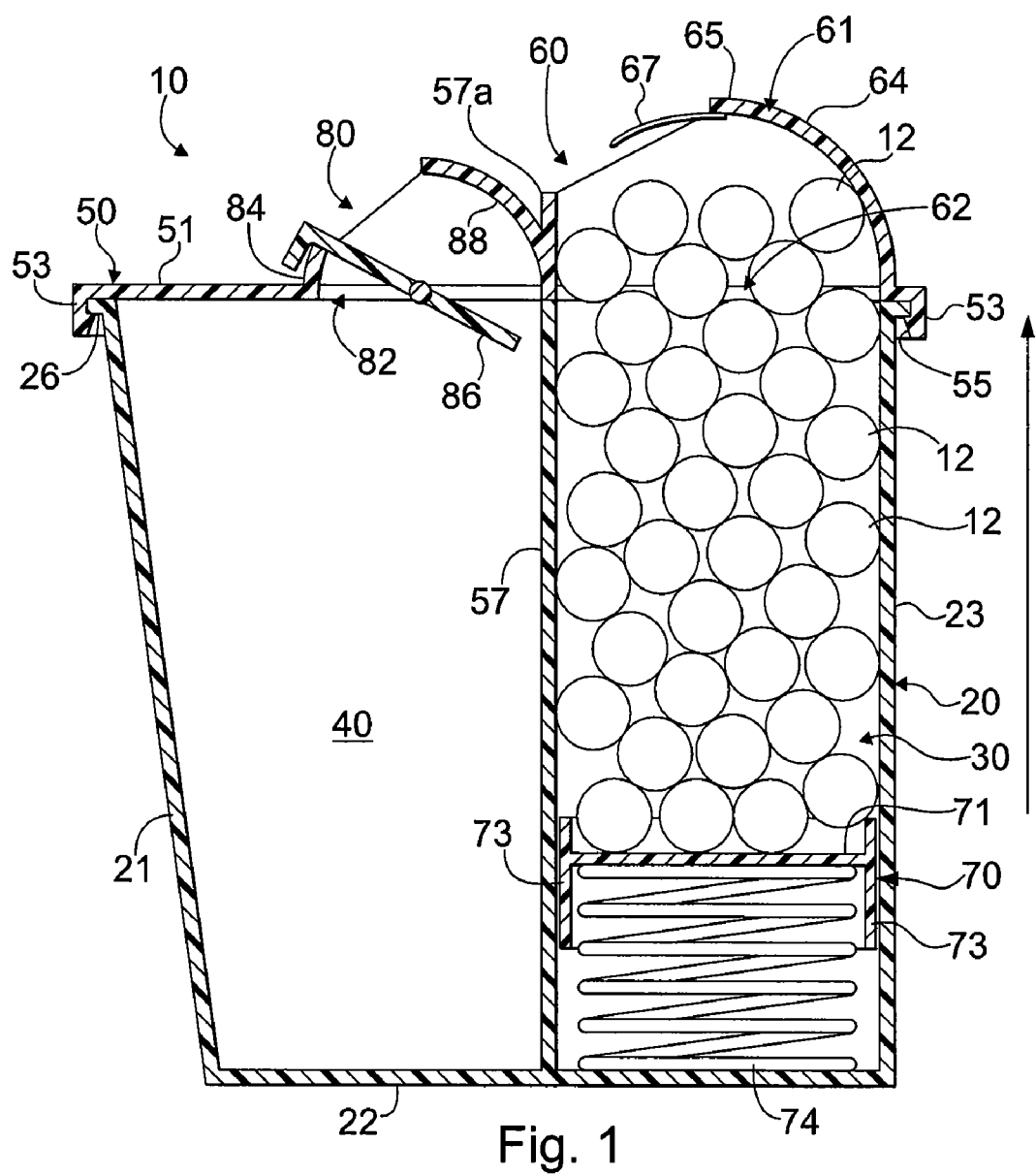
FIG. 1 is a side cross-sectional view of a medical implement dispensing and disposal system in accordance with an exemplary embodiment of the invention, the sharps dispensing and disposal system in an initial delivery state.

Although the invention is illustrated and described herein with reference to specific embodiments, the invention is not intended to be limited to the details shown. Rather, various modifications may be made in the details within the scope and range of equivalents of the claims and without departing from the invention. The invention is best understood from the following detailed description when read in connection with the accompanying drawing figures, which show exemplary embodiments of the invention selected for illustrative purposes. The invention will be illustrated with reference to the figures. Such figures are intended to be illustrative rather than limiting and are included herewith to facilitate the explanation of the present invention.

As used herein, the term medical implement refers to any commonly consumed device used for medical purposes, such as but not limited to a sharp, syringe, tongue depressor, lancet, scalpel, slide, pipette and the like.

Referring to FIGS. 1-4, a medical implement dispensing and disposal system 10 in accordance with an exemplary embodiment of the invention is shown. The medical implement dispensing and disposal system 10 is configured to both store unused medical implements and collect soiled medical implements. The medical implement dispensing and disposal system 10 generally includes a container 20 and a cover 50. As described in more detailed below, the container 20 of the present embodiment provides both a dispensing chamber 30 and a disposal chamber 40. Similarly, the cover of the present embodiment provides both a dispensing opening 60 and a disposal opening 80.

The container 20 and the cover 50 are preferably formed of puncture resistant material(s) suitable for the safe disposal and storage of sharps. In addition, the components are preferably formed of a resilient flexible material. Polypropylene provides one example of a material that can provide suitable puncture resistance and flexibility.

The container 20 has a bottom surface 22 with a front wall 21, a rear wall 23 and opposed side walls 25 extending therefrom. The walls 21, 23 and 25 define an open end 24 opposite the bottom surface 22. A rim 26 or the like may extend from the walls 21, 23, 25 about the open end 24. A divider wall 28 extends from the bottom surface 22 between the opposed side walls 55 and divides the container 20 into the dispensing chamber 30 and the disposal chamber 40. The divider wall 28 desirably extends the height of the container 20 such that the open end 24 is divided into a dispensing chamber opening 32 and a disposal chamber opening 42. The divider wall 28 is desirably formed integrally with the container 20, but may be formed as a separate component that is positioned within the container 20.

In a preferred embodiment, the cover 50 securely connects onto the container 20 and requires minimal assembly. In the present embodiment, the cover 50 is formed of polypropylene and includes a generally rectangular deck 51 that is generally the shape of and covers the container open end 24. A skirt 53 depends from the deck 51 and extends about the container rim 26 when the cover 50 is positioned on the container 20. The skirt 53 includes a tabbed edge 55 that fits around the underside of the container rim 26 and thereby secures the cover 50 to the container 20. Other connection mechanisms may also be utilized.

A pair of through holes 62 and 82 are defined through the deck 51 and are configured to align with the dispensing chamber 30 and the disposal chamber 40, respectively. In the present embodiment, an intermediate wall 57 extends across the deck 51 to divide the through holes 62 and 82. The through hole 62 aligned with the dispensing chamber 30 preferably has a width equal to the width of the dispensing chamber 30, while the through hole 82 aligned with the disposal chamber 40 has a width less than the width of the disposal chamber 40. Other sizes and configurations may also be utilized.

Figure 2:
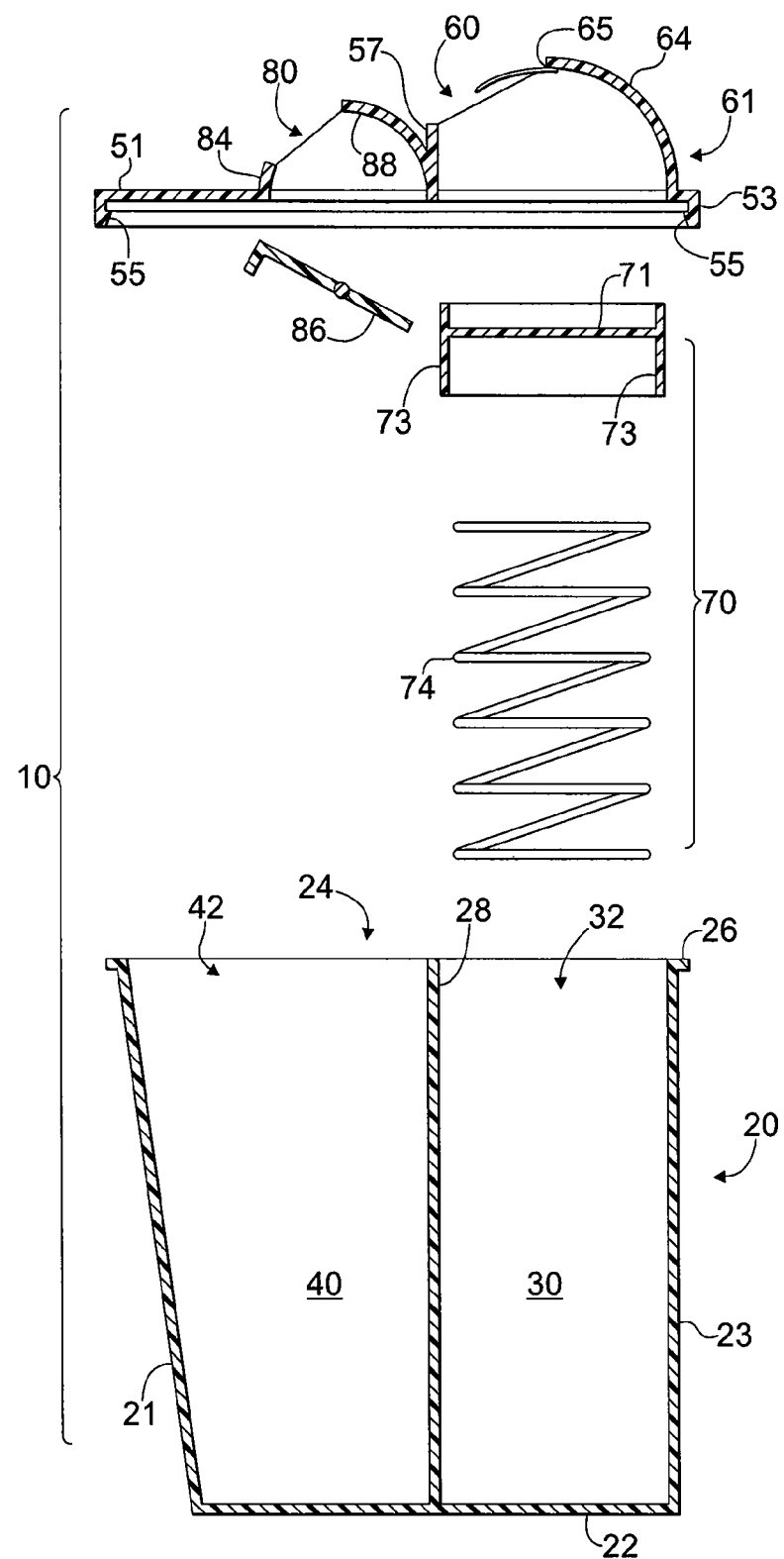
FIG. 2 is an exploded side cross-sectional view of the medical implement dispensing and disposal system of FIG. 1.
Figure 3:
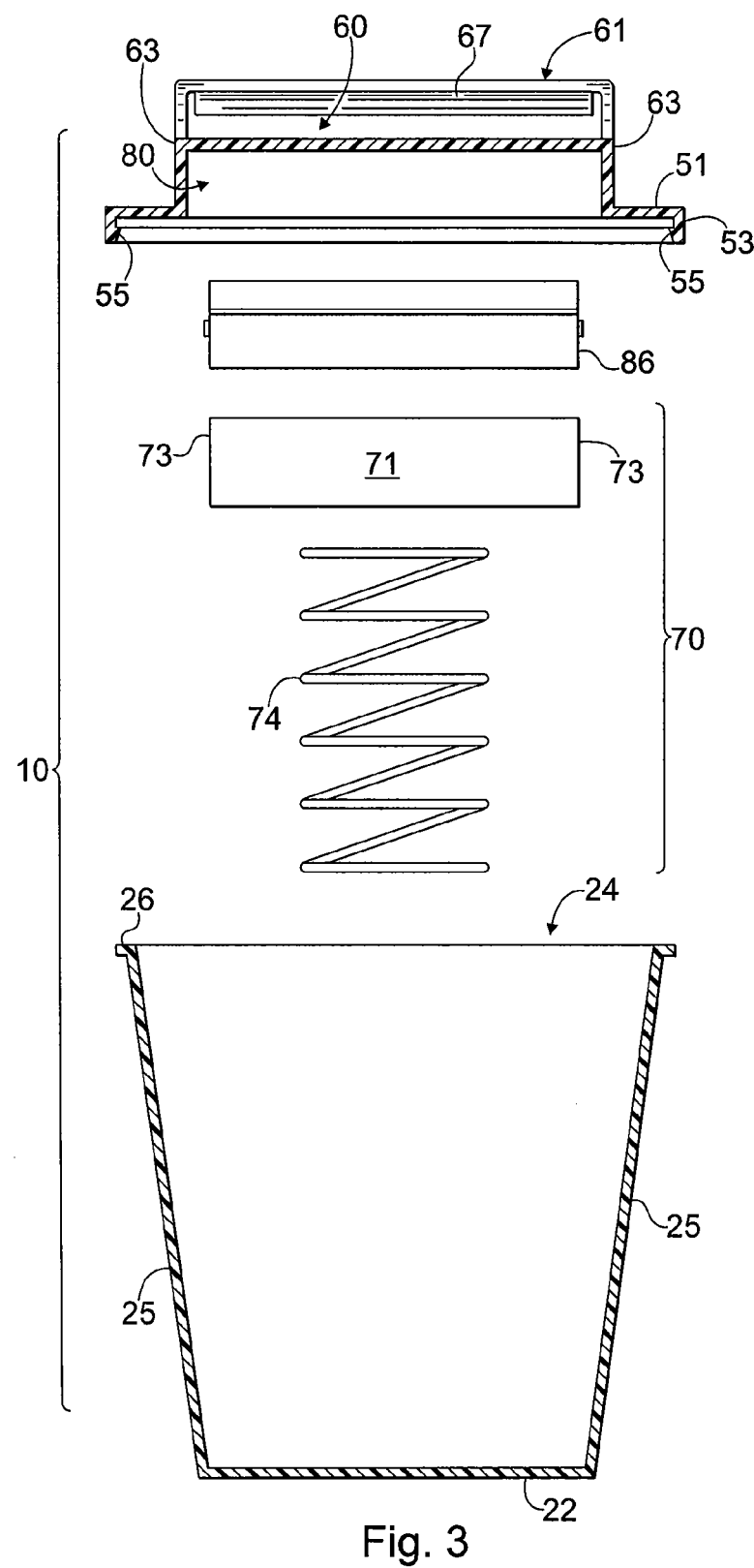
FIG. 3 is an exploded front cross-sectional view of the medical implement dispensing and disposal system of FIG. 1.

The cover 50 further defines the dispensing opening 60 and the disposal opening 80. The dispensing opening 60 is defined between the intermediate wall 57 and a hood component 61. As illustrated in FIGS. 2 and 3, the hood component 61 includes a curved surface 64 extending from the deck 51 along the rear edge of through hole 62 and terminating in a forward edge 65 and a pair of side walls 63 extending between the lateral edges of the curved surface 64 and the deck 51. The dispensing opening 60 is defined between the curved surface forward edge 65, the side walls 63 and an upper end 57A of intermediate wall 57. The dispensing opening 60 is preferably sized to facilitate passage of variously sized medical implements.

A flexible flap 67 extends from the curved surface forward edge 65 across the dispensing opening 60 to reduce the size of the opening to a width less than a width of the medical implements to be dispensed. To dispense an unused medical implement 12, a user must pull on the medical implement 12, thereby causing the flap 67 to flex outward to facilitate passage of the implement 12.

As illustrated in FIG. 1, the cover 50 defines a chute from the through hole 62 to the dispensing opening 60, such that unused medical implements 12 stored in the dispensing chamber 30 may easily pass through the hole 62 and be accessible through the dispensing opening 60. To maintain a supply of unused medical implements 12 available at the dispensing opening 60, a biased platform assembly 70 is positioned in the bottom of the dispensing chamber 30. In the present embodiment, the biased platform assembly 70 includes a horizontal platform 71 which extends substantially across the dispensing chamber 30. A pair of opposed vertical sides 73 extend from the platform 71 and ride along the rear wall 23 and intermediate wall 57 to guide vertical movement of the platform 71 within the chamber 30. A spring 74 or the like extends between the platform 71 and the container bottom surface 22 and biases the platform 71 upward toward the dispensing opening 60. As such, unused implements 12 positioned in the dispensing chamber 30 above the platform 71 are biased toward the dispensing opening 60. Other biasing elements other than a spring may alternatively be utilized. The rigidity of the flexible flap 67 and the biasing force of the spring 74, or other biasing element, are coordinated such that the biasing force does not cause implements 12 to be inadvertently dispensed through the dispensing opening 60.

Figure 5:
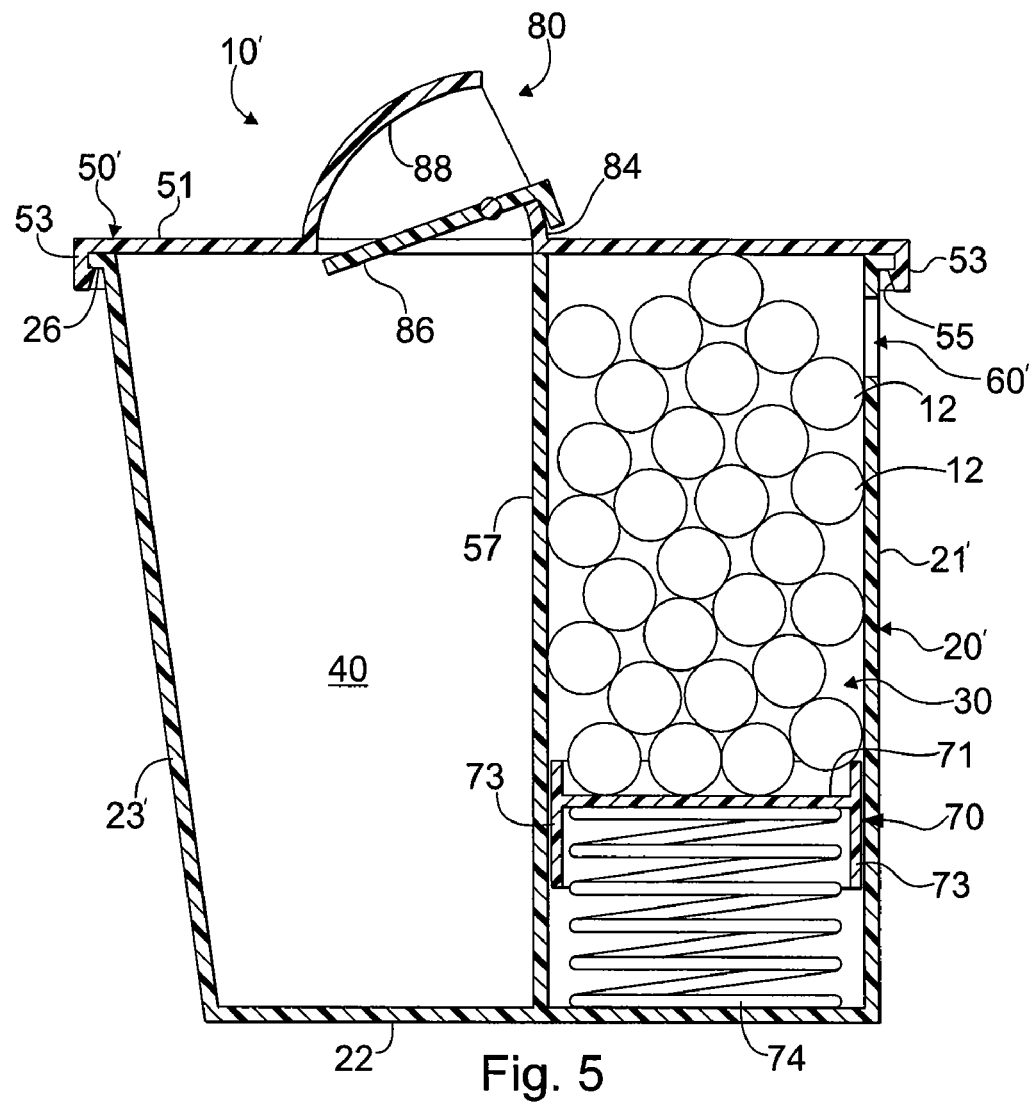
FIG. 5 is a side cross-sectional view of a medical implement dispensing and disposal system in accordance with another exemplary embodiment of invention.

The dispensing opening 60 is not limited to the cover 50. In the exemplary embodiment of the medical implement dispensing and disposal system 10' illustrated in FIG. 5, the dispensing opening 60' is provide through the front wall 21' of the container 20'. The cover 50' does not include a second through hole, but instead covers and closes off the dispensing chamber 30. In all other aspects, the medical implement dispensing and disposal system 10' of FIG. 5 is the same as in the previous embodiment.

Figure 4:
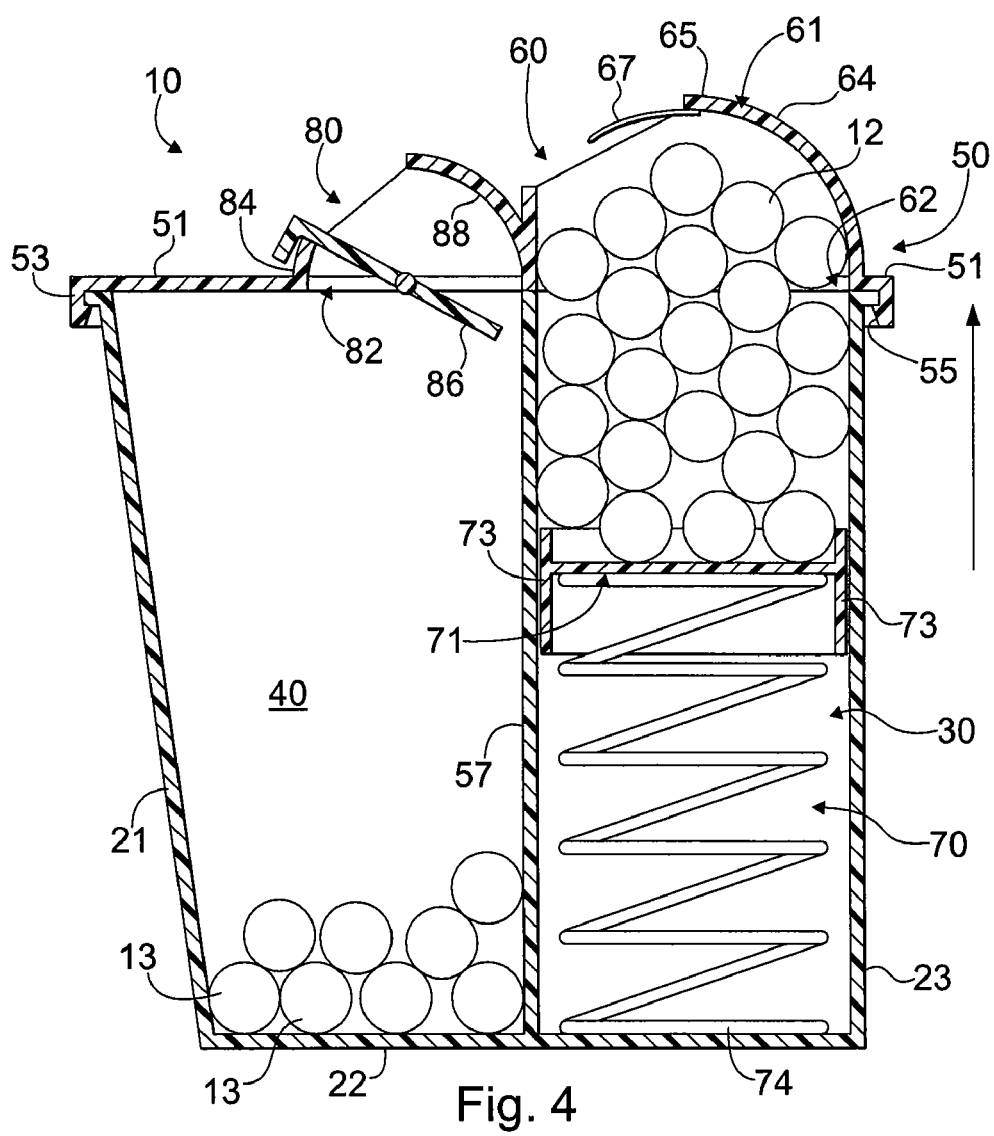
FIG. 4 is a side cross-sectional view similar to FIG. 1 with the medical implement dispensing and disposal system in a partially used state.

As explained above, the cover 50 also defines a disposal opening 80 which is configured to receive used medical instruments 13 which are passed through hole 82 into the disposal chamber 40, as illustrated in FIG. 4. The disposal opening 80 is defined between a pair of opposed hood components 84 and 88. The hood components 84 and 88 each desirably have a curved surface with opposed side walls, but other structures may also be utilized. A pivoting door 86 forms a surface for receiving sharps in a generally horizontal orientation. The door 86 is pivotally mounted inside hood 88 by pins or the like. In this arrangement, the door 86 is configured to tilt in response to a used medical implement being placed onto the door 86, for example at a position offset from the door's center of gravity, at which time the door 86 pivots and drops the used medical implement 13 through the hole 82 and into the disposal chamber 40 of the container 20. While a pivoting door system is described herein, the invention is not limited to such and other types of sharps disposal openings configured to provide a tortuous path opening may be utilized.

While the system 10 is described with the dispensing chamber 30 in the rear of the container 20 and the disposal chamber 40 in the front of the container, such may be reversed, with the cover 50 correspondingly adjusted. For example, the flexible flap may be provided along a forward edge of hood component 88 while the pivoting door 86 may be provided within the hood component 61. In such an embodiment, the biasing assembly 70 would be positioned in the front dispensing chamber 30. Other configurations may also be utilized, including side-by-side chambers.

System 10 is intended for use as a stationary dispensing/disposal container or a transportable handheld container. A variety of sizes are contemplated, such as a 2-quart hand held container or a 20-gallon wall-mounted container. Smaller or larger volumes may also be used, however. For smaller container systems, the container 20 or cover 50 may have an external geometry suitable for gripping and carrying of the system.

What is claimed:

1. A medical implement dispensing and disposal system comprising:
    a container having an open end with a dispensing chamber and a disposal chamber defined within the container for accommodating a plurality of medical implements;
    a cover configured to substantially close the open end of the container, the cover defining a disposal opening and a through hole and including a hood component, wherein the hood component defines a dispensing opening in communication with the dispensing chamber through the through hole, and the disposal opening is in communication with the disposal chamber; and
    a biasing assembly positioned in the dispensing chamber and configured to provide a biasing force to the medical implements in a general direction toward the dispensing opening.

2. The medical implement dispensing and disposal system of claim 1 wherein the container includes a bottom surface with a front wall, a rear wall and opposed side walls extending therefrom, and wherein an intermediate wall extends between either the opposed side walls or between the front and rear walls to define the dispensing and disposal chambers.

3. The medical implement dispensing and disposal system of claim 1 wherein the biasing assembly includes a platform positioned within the dispensing chamber.

4. The medical implement dispensing and disposal system of claim 3 wherein a biasing member is positioned between a bottom surface of the container and the platform.

5. The medical implement dispensing and disposal system of claim 1 including a plurality of medical implements within the disposal chamber defined within the container.

6. The medical implement dispensing and disposal system of claim 1, wherein the cover includes a flexible flap extending across at least a portion of the dispensing opening.

7. The medical implement dispensing and disposal system of claim 6, wherein the flexible flap has a rigidity greater than the biasing force.

8. The medical implement dispensing and disposal system of claim 1 wherein the medical implement may be a sharp, syringe, tongue depressor, lancet, scalpel, slide or pipette.

9. The medical implement dispensing and disposal system of claim 1 wherein the disposal opening includes a tortuous path into the disposal chamber.

10. The medical implement dispensing and disposal system of claim 9, wherein the tortuous path is defined in part by a pivotal door supported by the cover.

11. A medical implement dispensing and disposal system comprising:
   a container having an open end with a dispensing chamber for accommodating at least one medical implement, and a disposal chamber defined within the container, the container defining a dispensing opening on a side thereof in communication with the dispensing chamber;
   a cover configured to substantially close the open end of the container, the cover defining a disposal opening in communication with the disposal chamber, wherein the disposal opening includes a tortuous path into the disposal chamber, the tortuous path being defined in part by a pivotal door supported by the cover; and
   a biasing assembly positioned in the dispensing chamber and configured to provide a biasing force to the at least one medical implement in an upward direction toward the dispensing opening and against a gravitational force acting on the at least one medical implement.

12. The medical implement dispensing and disposal system of claim 11 wherein the container includes a bottom surface with a front wall, a rear wall and opposed side walls extending therefrom, and wherein an intermediate wall extends between either the opposed side walls or between the front and rear walls to define the dispensing and disposal chambers.

13. The medical implement dispensing and disposal system of claim 11 wherein the biasing assembly includes a platform positioned within the dispensing chamber.

14. The medical implement dispensing and disposal system of claim 13 wherein a biasing member is positioned between a bottom surface of the container and the platform.

15. The medical implement dispensing and disposal system of claim 11 wherein the medical implement may be a sharp, syringe, tongue depressor, lancet, scalpel, slide or pipette.

16. The medical implement dispensing and disposal system of claim 11 including a plurality of medical implements within the disposal chamber defined within the container.

\* \* \* \* \*